Figure 1:
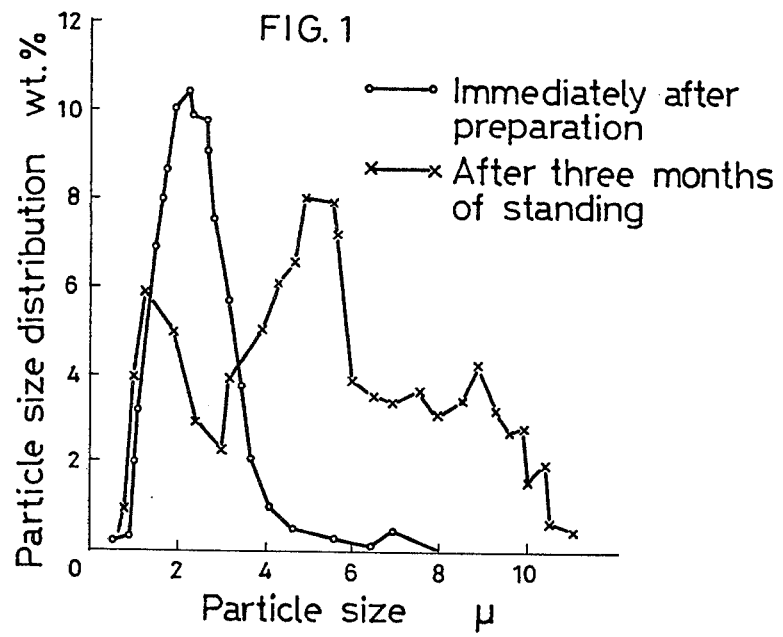

United States Patent [19]

Sezaki et al.

[11] 4,011,661
[45] Mar. 15, 1977

[54] POWDERED EMULSION PRODUCT AND METHOD OF PRODUCTION

[75] Inventors: Hitoshi Sezaki; Shozo Muranishi, both of Kyoto, Japan

[73] Assignee: Kyowa Hakko Kogyo Co., Ltd., Tokyo, Japan

[22] Filed: Dec. 15, 1975

[21] Appl. No.: 640,843

Related U.S. Application Data

[63] Continuation of Ser. No. 519,048, Oct. 29, 1974, abandoned.

[30] Foreign Application Priority Data

Oct. 30, 1973  Japan .......................... 48-121929
Oct. 30, 1973  Japan .......................... 48-121930

[52] U.S. Cl. .................................. 34/12; 34/9; 34/10
[51] Int. Cl.² .................................. F26B 7/00
[58] Field of Search ................. 34/9, 10, 12, 17

[56] References Cited
UNITED STATES PATENTS 3,521,370   7/1970   Senatore ........................... 34/10 X

*Primary Examiner*—John J. Camby
*Attorney, Agent, or Firm*—Fitzpatrick, Cella, Harper & Scinto

[57] ABSTRACT

Powdered products containing a drug or nutrient suitable for administering in emulsion form are prepared by dispersing (a) an oil; (b) a solution of a drug or nutriment in oil; or (c) an emulsion of an aqueous solution of a drug or nutriment in oil, in an aqueous solution containing a surface layer former, and, where appropriate, a drug or nutriment, and then spray-drying the dispersion.

6 Claims, 2 Drawing Figures

POWDERED EMULSION PRODUCT AND METHOD OF PRODUCTION

This is a continuation of application Ser. No. 519,048, filed Oct. 29, 1974, now abandoned.

BACKGROUND OF THE INVENTION

The present invention relates to a powdered product suitable for the preparation of emulsions, and more specifically, to a powdered product prepared by dispersing (a) an oil; (b) a solution of a drug or nutriment in oil; or (c) an emulsion of an aqueous solution of a drug or nutriment in oil, in an aqueous solution containing a surface layer former and, where appropriate a drug or nutriment, and then spry-drying the resulting dispersion.

Heretofore, there have been known water-in-oil emulsion products prepared by emulsifying an aqueous solution of a water-soluble drug in oil. Also, there have been reports of water-in-oil-in-water emulsion products obtained by further emulsifying the water-in-oil emulsion in water.

Such products have been frequently used in the clinical administration of a drug or nutriment together with a suitable oil. For example, where an emulsion of an aqueous solution of an anti-cancer substance such as 5-fluorouracil, bleomycin and mitomycin C, and an oil is administered, the drug has a lymphatic directivity due to the property of the co-existing oil. Therefore, the drug selectively reaches the lymph nodes at a high concentration. Such characteristic is of great importance in administering an anti-cancer substance for the treatment of metastases of cancer to lymph nodes. In addition, where an analgesic, an antibiotic or the like is incorporated into fine particles of an oil and such is administered by injection, where the size of the particle of oil is larger than a predetermined certain size, the particle is maintained in the capillary vessels. In this case, the active ingredient, i.e. the drug, gradually permeates into the surrounding tissues. Therefore, the concentration of the drug in the specific tissue can be maintained at a high level for a long period of time. This apparently results in an enhanced durability of the effect of the drug. Moreover, it can easily be understood that such method would be effective to administer an oil together with nutriments such as amino acids and glucose to a patient who has undergone a surgical operation. In addition, it is possible in such manner to administer an oil itself, as a nutriment, in the form of an emulsion.

From the foregoing, it will be understood that a double emulsion of a water-in-oil emulsion in water or an oil-in-water emulsion is very useful. However, the stability of the emulsion per se or that of drugs or nutriments is not at all satisfactory. More specifically, when an emulsion once prepared is preserved for a long period of time, the emulsion structure is destroyed thus separating into oil and water. Moreover, the drug or nutriment which is an active ingredient is not necessarily stable.

FIG. 1 of the drawing shows test results at different time periods; and

Figure 2:
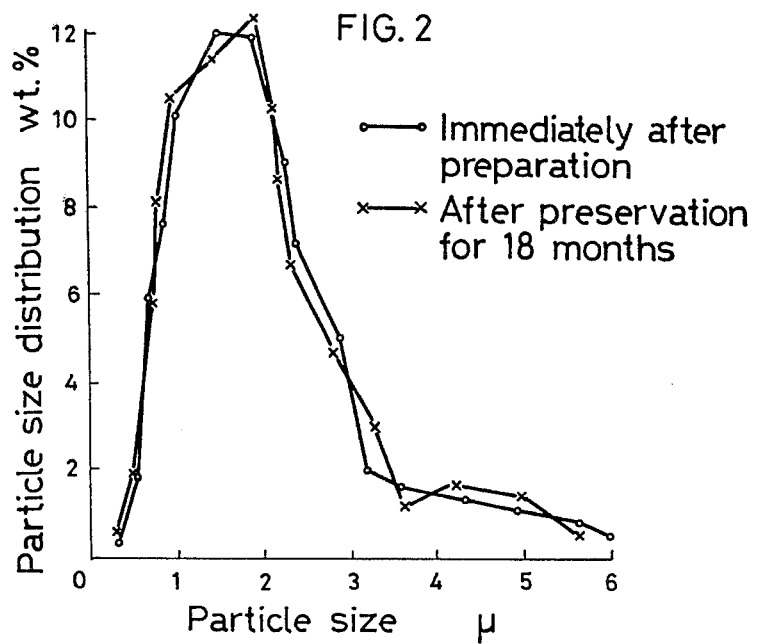

FIG. 2 shows other test results at different time periods.

To illustrate, the stability of an oil-in-water emulsion is examined. An emulsion is prepared by adding sesami oil to a solution of mitomycin C in benzylalcohol and emulsifying the mixture in water in a ratio of 1:4. The particle size distribution of the thus prepared oil-in-water emulsion is measured with a coal tar counter immediately after the preparation thereof and again after three months of standing at room temperature. The results are shown in FIG. 1 wherein, the horizontal axis shows the particle size ($\mu$) and the vertical axis shows the particle size distribution (%). As is apparent from FIG. 1, after three months of standing, the particle size becomes extremely ununiform.

Further, the stability of mitomycin C in an oil-in-water emulsion prepared in the same manner as above is tested. The results are shown in Table 1 below.

Table 1

| | Residual ratio (%) Period after preparation (days) | | | | | |
|---|---|---|---|---|---|---|
| Concentration | 2 | 4 | 9 | 16 | 23 | 43 |
| 20 mg/100ml | 81.0 | 73.4 | 62.7 | 45.7 | 29.8 | 22.4 |
| 30 mg/100ml | 82.9 | 71.9 | 65.2 | 55.1 | 36.9 | 32.6 |
| 40 mg/100ml | 86.5 | 78.1 | 69.4 | 59.5 | 41.6 | 36.3 |

As is apparent from the foregoing Table 1, mitomycin C rapidly decomposes.

In efforts to solve the problems exemplified by the above, it has been proposed to prepare the emulsion just prior to administration. However, the preparation of an emulsion requires sophisticated equipment and is time consuming; and is thus impractical for general use. It has also been proposed to prepare a solution of a drug in oil or an emulsion of an aqueous solution of drugs in oils into microcapsules and to emulsify the microcapsules in water just prior to administration. However this proposal also suffers from various disadvantages. The preparation of microcapsules also requires complicated steps and it is difficult to obtain microcapsules as small as several microns. Moreover, the use of microcapsules suffers from the disadvantage that the same do not readily decompose upon reaching the capillary vessels.

Therefore, improvements are in great demand.

SUMMARY OF THE INVENTION

In accordance with the present invention, it has been found that a powdered product, prepared by emulsifying (a) an oil, (b) a solution of a drug or a nutriment in oil or (c) an emulsion of an aqueous solution of a drug or a nutriment in oil, in (d) water containing a surface layer former or (e) an aqueous solution of a drug or nutriment containing a surface layer former and thereafter spry-drying the resulting emulsion or double emulsion, is very advantageous. The powdered product is characterized by a structure in which the surface of a small particle of oil, a solution of the drug or nutriment in oil or the water-in-oil emulsion of the drug or nutriment is coated with a thin layer of a skin former. The product appears to be a powder or a small mass of powder.

Depending on the particular method of preparation, it is considered that the drug or nutriment in the aqueous solution is present mainly between the surface of the particle of oil and the thin layer of the surface layer former, combined with the oil. In certain applications it is also considered that some portion of the aqueous solution is incorporated as it is into the oil as fine particles.

The product of the present invention is, of course, stable in structure. In addition, the drug or nutriment incorporated therein is also very stable and and can be preserved for a long period of time.

The product of the invention can easily be prepared into an oil-in-water emulsion or a double emulsion of water-in-oil-in-water again by mixing with an appropriate amount of water and the resulting emulsion is ready for administration. Furthermore, when the product of the invention is used, an emulsion contaning particles of a desired size in a range between one micron and several hundred microns and at the same time having a small particle size distribution can be prepared.

DESCRIPTION OF THE INVENTION

In accordance with the present invention a powdered product is prepared which is suitable for emulsifying on short notice and subsequent administration.

In one form of the invention, an aqueous solution of a drug or nutriment to be employed is prepared. The concentration is properly selected depending upon the solubility of the specific drug or nutriment or the desired dosage thereof. Where the water-solubility of the drug or nutriment is poor, it may be first dissolved in a water-miscible solvent and then the solution may be mixed with water. For the preparation of the aqueous solution, buffer solutions such as tris-buffer, etc. and physiological sodium chloride solution may be used in addition to distilled water.

A surface layer former is then dissolved in the aqueous solution. Any surface layer former may be used as long as it can form a thin layer, is water-soluble and causes no inconvenience upon administration. For example, gelatin, polyvinylpyrrolidone, methylcellulose, polyvinyl-alcohol, polyethylene glycol and fatty acid esters of sucrose are appropriate. The concentration of the surface layer former is 0.5% – 10% by weight, preferably, 1% – 3% by weight based upon the weight of oil and water.

Then, an oil is dispersed in the thus prepared aqueous solution to prepare an emulsion. Appropriate oils include peanut oil, olive oil, vitamin A oil and vitamin E oil but the use of sesame oil is most practical and is thus preferred. The mixing ratio of the oil to the aqueous solution is 1:1 – 1:40, preferably, 1:4 – 1:5. In preparing the emulsion, if desired, a stabilizer for the drug or nutriment to be employed may be added. Additionally, an emulsifier such as surfactants and other additives may also be added. Appropriate surfactants include cationic surfactants such as benzethonium chloride, benzalkonium chloride, etc., anionic surfactants such as sodium laurylsulfate, etc., and nonionic surfactants such as polyoxyethylene fatty acid ester, polyoxyethylene sorbitan fatty acid ester, etc.

Emulsification may be carried out either by adding the oil to an aqueous solution containing the surface layer former and the drug or nutriment with vigorous stirring, or by adding the aqueous solution to the oil. An emulsifier may be added either to the aqueous solution or to the oil. As an homogenizer, any of the commercially available homogenizers may be employed. If necessary, heating or cooling is applied during emulsification to obtain a uniform emulsion. In this emulsification step, the particle size of the oil is adjusted by selecting the stirring conditions, temperature and kind or concentration of the surface layer former. The adjustment of particle size can be carried out in a conventional manner known in the art. The thus obtained emulsion is then spray-dried. The conditions of spray-drying may be selected depending upon the kind and concentration of the drug nutriment, oil or the other raw materials to be employed or the size of particles in the emulsion. However, usually, the spray-drying step is carried out at an inlet-gas temperature of 100°–200° C and an outlet-gas temperature of 70°–100° C. Spray-drying is accomplished by means of commercial devices known to the art. For example, a cylinder spray drier or cyclone spray drier provided with an atomizer of pressure nozzle type, centrifugal disk type or two-fluid nozzle type may be used. When a spray drier having a centrifugal disk type-atomizer is used, spray-drying is carried out usually at a rotation of the atomizer of 10,000–25,000 r.p.m.

In this form of the invention, it is to be understood that an oil-soluble drug or nutriment may be dissolved in oil at an appropriate concentration and emulsified in water containing the surface layer former.

In another form of the invention, a powdered product of a double emulsion of a water-in-oil emulsion of an aqueous solution of drugs or nutriments in oil in water is prepared in the following manner.

First, an aqueous solution of a drug or nutriment is prepared. The concentration is properly selected depending upon the solubility of the drug or nutriment to be employed or the desired dosage thereof. It is to be understood that there is no restriction on the concentration of the drug or nutriment and such is variable depending upon the desired result. For the preparation of the aqueous solution, buffer solutions such as tris-buffer, etc. and physiological sodium chloride solution may be used in addition to distilled water.

The aqueous solution prepared above is then dispersed and emulsified in oil, such as peanut oil, olive oil, vitamin A oil and vitamin E oil, preferably sesami oil. The mixing ratio of the oil to the aqueous solution of the drug or nutriment is 1:10 – 1:1, preferably 1:6 – 1:4. In preparing the water-in-oil emulsion, if desired, a stabilizer for the drug or nutriment to be employed may be added. Further, an emulsifier such as the above-described surfactants and other additives may also be added.

The water-in-oil emulsion prepared in this manner is then mixed with an aqueous solution containing a surface layer former and re-emulsified to prepare a water-in-oil-in-water emulsion. The mixing ratio of the water-in-oil emulsion to the aqueous solution is 1:1 – 1:10, preferably 1:2 – 1:3. The surface layer former may be the same as those described above and the concentration of the surface layer former is also the same as above. It is to be understood that such emulsifiers as surfactants, and other additives may, of course, be added when the re-emulsification is carried out and particle size is adjusted during the preparation of the double emulsion.

The emulsification to prepare the water-in-oil emulsion and the double emulsion of water-in-oil-in-water is carried out in the same manner as described above for the preparation of the emulsion of oil in water.

The emulsion thus prepared is a double emulsion which has a structure characterized by small particles, each comprising a particle of an aqueous solution of a drug or nutriment coated with oil, dispersed in an aqueous solution containing a surface layer former.

By spray-drying the double emulsion, the desired powdered product is obtained. The spray-drying can be carried out under the same conditions as those for the preparation of the powdered product described above.

The products of the present invention are very stable and can be preserved for a long period of time. The products are readily prepared as an oil-in-water emulsion or water-in-oil-in-water emulsion again by simply mixing with water. The emulsion is very stable and can be maintained for a long period of time.

For example, a powder having an average particle size of 15 $\mu$ and comprising sesami oil coated with 20% by weight of gelatin based on the weight of sesami oil is physically and chemically very stable. After standing at room temperature for 18 months, the powder undergoes no change in appearance and in particle size distribution when dispersed in water. To disperse the powder in water 3 g of the powder and 20 ml of water are placed in a 50 ml-centrifugal precipitation tube having an inner diameter of 3 cm closed with an air-tight ground stopper. Reciprocal shaking is applied at an amplitude of 4 cm and at a frequency of 280 times per min.; and the time required for complete restoration to an emulsion is measured. The test is conducted immediately after the preparation of the powdered product and after 30 days, 12 months and 18 months of preservation. The powder is restored to an emulsion within 2 minutes in each case.

The particle size distribution of the powder is measured immediately after the preparation and after preservation for 18 months. The results are shown in FIG. 2 wherein the horizontal axis shows the particle size ($\mu$) and the vertical axis shows particle size distribution (%). As is apparent from FIG. 2, no substantial change appears in the particle size distribution.

To further exemplify the stability of a product prepared in accordance with the present invention, a powdered product having an average particle size of 12 $\mu$ and comprising a gelatin-coated sesami oil containing 2mg/g of mitomycin C is stored under shaded conditions for one year and the content of mitomycin C in the product is periodically measured. The results are shown in the following Table 2.

Table 2

| Sample No. | Immediately after preparation | Content (mg/g) Period of preservation (days) | | | |
|---|---|---|---|---|---|
| | | 30 | 90 | 180 | one year |
| 1 | 2.12 | 2.08 | 2.06 | 2.01 | 2.00 |
| 2 | 2.08 | 2.10 | 2.01 | 2.01 | 1.98 |
| 3 | 2.03 | 2.02 | 2.00 | 1.98 | 1.96 |

As is apparent from Table 2, mitomycin C in the product is very stable.

In preparing a powdered product of the present invention, it is, of course, possible to employ the oil, drug and nutriment as a mixture of two or more constituents. It is also possible within the scope of the present invention to prepare a product containing an oil-soluble drug and a water-soluble drug. Such product can be prepared by dissolving an oil-soluble drug in oil and a water-soluble drug in water; mixing and emulsifying the solution; dispersing the emulsion in water to prepare a double emulsion; and spray-drying the double emulsion.

When the product of the present invention is prepared into an emulsion for administration, an aqueous solution containing nutriments such as glucose, amino acids, etc. and other drugs may be employed.

In addition to the above, various modifications are possible for the production and use of the product of the present invention. Such modifications will be apparent to those skilled in the art.

Practice of certain specific embodiments of the invention is illustrated by the following representative examples.

EXAMPLE 1

In this example 1.5 l. of sesami oil, 3 l. of distilled water and 3 l. of an aqueous 10% solution of gelatin are mixed and emulsified with a supersonic apparatus under ice-cooling. The resulting oil-in-water emulsion is subjected to spray-drying in a cyclone spray drier having a diameter of 1.6 m provided with a disk type-atomizer, at a rotation of 15,000 r.p.m. and at an inlet-gas temperature of 150° C and an outlet-gas temperature of 90° C. As a result, 1.2 kg of a fine powder having an average particle size of 1.5 $\mu$ is obtained. Upon mixing 10 g of the powder with 40 ml of water, the powder is immediately restored to an emulsion.

EXAMPLE 2

In this example, 1.5 l. of peanut oil, 3 l. of distilled water and 3 l. of an aqueous 10% solution of polyvinylpyrrolidone are treated in the same manner as described in Example 1. As a result, 1.3 kg of a fine powder having an average particle size of 2 $\mu$ is obtained. By mixing 10 g of the powder with 40 ml of water, the product is readily restored to an emulsion.

EXAMPLE 3

In this example, 1.5 l. of sesami oil, 3 l. of distilled water, 3 l. of an aqueous 10% solution of gelatin and 60 g of Tween 80 (trade name of Atlas Chemical Industries Inc., U.S.A.) are treated in the same manner as described in Example 1. As a result, 1.3 kg of a fine powder having an average particle size of 2 $\mu$ is obtained. By mixing 10 g of the powder with 40 ml of water, the powder is readily restored to an emulsion.

EXAMPLE 4

In this example, 500 g of tocopherol is dissolved in 1.5 l. of sesami oil. The solution is mixed with 3 l. of distilled water, 3 l. of an aqueous 10% solution of gelatin and 60 g of Tween 80 and the mixture is emulsified with a supersonic apparatus under ice-cooling. The resulting oil-in-water emulsion is subjected to spray-drying at an inlet-gas temperature of 100° C and an outlet-gas temperature of 80° C. As a result, 1.8 kg of a fine powder having an average particle size of 5 $\mu$ is obtained. By mixing 0.2 g of the powder with 10 ml of water, the product is readily restored to an emulsion.

EXAMPLE 5

In this example, the procedure described in Example 4 is repeated except for using olive oil in place of sesami oil and methylcellulose in place of gelatin. As a result, 1.8 kg of a powdered product having an average particle size of 6 $\mu$ is obtained. The product is readily restored to an emulsion upon mixing with water.

EXAMPLE 6

In this example, 8.25 l. of sesami oil, 60 g of Span-80 (trade name of Atlas Chemical Industries, U.S.A.) and 15 g of HCO-60 (trade name of Nikko Chemical Co., Ltd. Japan for a surfactant comprising polyoxyethylene hydrogenated caster oil) are mixed. To 2 l. of the mixture is added 350 ml of an aqueous solution containing 175 mg. of mitomycin C and the mixture is emulsified with a supersonic apparatus at 50° C. Then 1 l. of the resulting water-in-oil emulsion is re-emulsified together with 1.6 l. of an aqueous 10% solution of gelatin with a homogenizer at 5,000 r.p.m. for 15 min. The resulting double emulsion is subjected to spray-drying at an inlet-gas temperature of 110° C and an outlet-gas temperature of 90° C. to obtain a powdered product having an average particle size of 20 $\mu$. By mixing 30 g of the powder with 100 ml of water, the product is restored to a water-in-oil-in-water emulsion.

EXAMPLE 7

In this example, a mixture consisting of 43.49% sesami oil, 40.21% of an aqueous solution containing 0.5 mg/ml of 5-fluorouracil and 4.42% portions of benzylalcohol, lecithin, sorbitan monooleate and sorbitan monostearate is emulsified into a water-in-oil emulsion using a supersonic apparatus. A mixture consisting of 37.25% emulsion thus obtained, 5.75% Pulronic F-68 (trade name of Wyandotte Chemicals Corporation, U.S.A.) and 57.0% distilled water is emulsified with a homogenizer at 7,000 r.p.m. for 15 min. to prepare a double emulsion. The resulting emulsion is then subjected to spray-drying at an inlet-gas temperature of 110° C and an outlet-gas temperature of 90° C to obtain a powdered product having an average particle size of 10 $\mu$.

EXAMPLE 8

In this example, the procedure described in Example 5 is repeated except for using bleomycin and mitomycin C, respectively, in place of 5-fluorouracil. As a result, powdered products containing the respective drugs are obtained.

EXAMPLE 9

In this example, 300 ml of an aqueous solution containing 250 mg of mitomycin C, 300 ml of an aqueous 10% solution of gelatin and 150 ml of sesami oil are mixed and emulsified with a supersonic apparatus under ice-cooling. The resulting emulsion is subjected to spray-drying in a cyclone spray drier having a diameter of 1.6 m provided with a disk type-atomizer, at a rotation of 10,000 r.p.m. and at an inlet-gas temperature of 160° C and a outlet-gas temperature of 80° C. As a result, 120 g of a fine powder having an average particle size of 2 $\mu$ is obtained. By mixing 3 g of the powder with 20 ml of water, the product is readily restored to an emulsion.

EXAMPLE 10

In this example, 300 ml of an aqueous solution containing 6 g of 5-fluororuracil, 300 ml of an aqueous 5% solution of polyvinylpyrrolidone and 150 ml of peanut oil are treated in the same manner as described in Example 9. As a result, 130 g of a powder having an average particle size of 5 $\mu$ is obtained. By mixing 2 g of the powder with 10 ml of water, the powder is readily restored to an emulsion.

EXAMPLE 11

In this example, 500 ml of an aqueous solution containing 10 g of chlorpromazine, 500 ml of an aqueous 5% solution of gelatin and 200 ml of sesami oil in which 20 g of polyoxyethylene sorbitan monooleate is dissolved are treated with a homogenizer at 10,000 r.p.m. for 15 min. The resulting emulsion is subjected to spray-drying at an inlet-gas temperature of 105° C and an outlet-gas temperature of 93° C. As a result, 200 g of a fine powder having an average diameter of 6 $\mu$ is obtained. The product is readily restored to an emulsion by mixing 2 g of the powder with 10 ml of water.

What is claimed is:

1. A method of preparing a powdered product suitable for preparing an emulsion which comprises: dispersing at least one substance selected from (a) a solution of a drug or nutriment in oil, or (b) an emulsion of an aqueous solution of a drug or nutriment in oil, in an aqueous solution containing 0.5–10.0% by weight of a surface layer former based on the total weight of oil and water and thereafter spray-drying the dispersion.

2. A method according to claim 1 wherein said oil is selected from the group consisting of sesami oil, peanut oil, olive oil, vitamin A oil and vitamin E oil.

3. A method according to claim 1 wherein said surface layer former is selected from the group consisting of gelatin, polyvinylpyrrolidone, methylcellulose, polyvinylalcohol, polyethylene glycol and fatty acid esters of sucrose.

4. A method according to claim 3 wherein the concentration of said surface layer former is from 1% to 3% by weight based upon the total weight of oil and water.

5. A method according to claim 1 wherein said spray-drying step is carried out at an inlet-gas temperature of 100°–200° C. and an outlet-gas temperature of 70°–100° C.

6. A powdered product prepared by the method of claim 1.

* * * * *